US012697504B2

(12) United States Patent (10) Patent No.: US 12,697,504 B2

Prindle et al. (45) Date of Patent: Aug. 4, 2026

(54) HEATED BRUSH WITH HOLLOW BRISTLES FOR AIR AND LIGHT APPLICATION

(71) Applicant: L'ANGE HAIR, INC., Chatsworth, CA (US)

(72) Inventors: Daniel Prindle, Dayton, OH (US); Wei Jin Tay, Centerville, OH (US); Amnon Hadari, Dania Beach, FL (US)

(73) Assignee: L'ANGE HAIR, INC., Chatsworth, CA (US)

( * ) Notice: Subject to any disclaimer, the term of this patent is extended or adjusted under 35 U.S.C. 154(b) by 217 days.

(21) Appl. No.: 18/461,160

(22) Filed: Sep. 5, 2023

(65) Prior Publication Data

US 2025/0073488 A1 Mar. 6, 2025

Related U.S. Application Data

(63) Continuation-in-part of application No. 29/911,533, filed on Sep. 5, 2023.

(51) Int. Cl.
| | |
|---|---|
| *A61N 5/06* | (2006.01) |
| *A45D 20/12* | (2006.01) |
| *A45D 20/50* | (2006.01) |
| *A46B 9/02* | (2006.01) |

(Continued)

(52) U.S. Cl.
CPC ........... *A61N 5/0617* (2013.01); *A45D 20/12* (2013.01); *A45D 20/50* (2013.01); *A46B 9/023* (2013.01); *A46B 15/0004* (2013.01); *A46B 15/0024* (2013.01); *A46B 15/003* (2013.01); *A46B 15/0034* (2013.01); *A46B 15/0051*

(2013.01); *A46D 1/0246* (2013.01); *A45D 2200/202* (2013.01); *A45D 2200/205* (2013.01); *A46B 2200/104* (2013.01)

(58) Field of Classification Search
None
See application file for complete search history.

(56) References Cited

U.S. PATENT DOCUMENTS

| | | | |
|---|---|---|---|
| 7,428,785 B2 | 9/2008 | Kim | |
| 7,584,759 B2 * | 9/2009 | Yasuda | ................... A45D 20/10 |
| | | | 34/97 |
| 10,398,218 B2 | 9/2019 | Exley | |

(Continued)

FOREIGN PATENT DOCUMENTS

| | | |
|---|---|---|
| CN | 209489639 U | 10/2019 |
| CN | 307777751 | 1/2023 |

(Continued)

OTHER PUBLICATIONS http://web.archive.org/web/20221102052121/https://langehair.com/ (Nov. 2, 2022).

(Continued)

*Primary Examiner* — Erica S Lee

(74) *Attorney, Agent, or Firm* — Sheppard, Mullin, Richter & Hampton LLP

(57) ABSTRACT

A brush for delivering at least one of an application of light and/or heat includes a handle and a head extending therefrom, a light emitting device and/or heating element and a plurality of hollow bristles extending from a surface of the head and receiving at least a portion of light and/or heated air or non-heated air through the bristles.

11 Claims, 7 Drawing Sheets

(51) Int. Cl.
*A46B 15/00* (2006.01)
*A46D 1/00* (2006.01)

(56) References Cited

U.S. PATENT DOCUMENTS

| | | | |
|---|---|---|---|
| D940,463 S | 1/2022 | Zhu | |
| D943,280 S | 2/2022 | Zou | |
| D946,899 S | 3/2022 | Yang | |
| 11,363,871 B2 | 6/2022 | Bridgett | |
| D970,893 S | 11/2022 | Hu | |
| D973,365 S | 12/2022 | Huen | |
| D973,956 S | 12/2022 | Du | |
| D975,918 S | 1/2023 | Yuan | |
| D1,003,608 S | 11/2023 | Yin et al. | |
| D1,024,578 S | 4/2024 | Moon et al. | |
| D1,050,590 S | 11/2024 | Lai et al. | |
| D1,055,530 S | 12/2024 | Yang et al. | |
| D1,069,238 S | 4/2025 | Wang | |
| 2005/0109755 A1 | 5/2005 | Rachel | |
| 2005/0251242 A1* | 11/2005 | Bousfield | A61N 5/0617 607/150 |
| 2007/0015112 A1* | 1/2007 | Hochman | A61B 8/546 433/215 |
| 2008/0177255 A1* | 7/2008 | Bernardini | A61N 5/0617 132/200 |
| 2014/0100489 A1* | 4/2014 | Altshuler | A61H 99/00 601/18 |
| 2018/0015299 A1* | 1/2018 | Kawa | A61N 1/326 |
| 2018/0042357 A1* | 2/2018 | Lescht | A45D 2/127 |
| 2020/0128935 A1 | 4/2020 | Turner | |
| 2022/0160576 A1* | 5/2022 | Kosecoff | A45D 24/22 |
| 2024/0057740 A1* | 2/2024 | Weatherly | A45D 20/50 |
| 2025/0073488 A1 | 3/2025 | Prindle et al. | |

FOREIGN PATENT DOCUMENTS

| | | |
|---|---|---|
| CN | 308211606 | 9/2023 |
| WO | WO 2005/102100 | 11/2005 |

OTHER PUBLICATIONS langehair.com/collectins/hot-brush.

"L'ange Hair", webpage <http://www.langehair.com>, 1 page, retrieved from Internet Archive Wayback Machine http://web.archive.org/web/20221102052121/https://langehair.com/.

L'Ange Hair AI Ress 2-in-1 Blow Dryer Brush, posted Oct. 13, 2023 [online], [retrieved Aug. 12, 2025]. Retrieved from internet, https:// www.amazon.com/dp/BOCKDS8B33/?th=1 (Year: 2023).

Newness has arrived, posted Sep. 6, 2023 [online], [retrieved Aug. 12, 2025]. Retrieved from internet, https://www.instagram.com/p/Cw26ahvpdvU# (Year: 2023).

Hot Brush, posting date unknown [online], [retrieved Aug. 12, 2025]. Retrieved from internet, https://langehair.com/collections/hot-brush (Year: 2025).

* cited by examiner

HEATED BRUSH WITH HOLLOW BRISTLES FOR AIR AND LIGHT APPLICATION

FIELD OF INVENTION

The invention relates to a heated hair brush with air and light application. More particularly, the invention relates to a heated hair brush which includes one or more heating components and a unique air and light application delivery aspect.

BACKGROUND OF THE DISCLOSURE

There exist numerous heated hair brushes and light therapies for hair and scalp. For example, the known devices include a housing that has a handle portion and a head portion and define a compartment wherein base plate is disposed at the head portion of the housing and has an upper face and one or more heating elements on the upper face to assist in drying hair. There also exists light devices integrated in the upper surface of a brush. The light treatment is intended to radiate a therapeutic light toward the scalp to assist in stimulating the hair follicles.

While these known devices provide some usefulness, there remains room for improvements to such hair brushes and light treatment to better aid the user in delivering an overall improved hair brush.

SUMMARY OF THE INVENTION

An object is to improve implement for hair styling and application.

Another object is improve a hair brush which delivers heated air to hair in a novel manner.

Still another object is improve a brush which uniquely delivers light to the hair and/or scalp through hollow bristles.

Another object is to provide adjustable air flow in a hair brush through hollow bristles.

Accordingly, one aspect of the disclosure provides a brush which includes a handle and a head extending therefrom, a light emitting device operably disposed in the head and a plurality of hollow bristles extending from a surface of the head and receiving at least a portion of light therethrough. Another aspect is to provide a heating element in the head and a blower operably connected to the brush to direct air flow through hollow bristles extending from the head. In a preferred embodiment, the brush is equipped to enable a selective amount of air flow through the bristles.

DETAILED DESCRIPTION OF THE INVENTION

Figure 1:
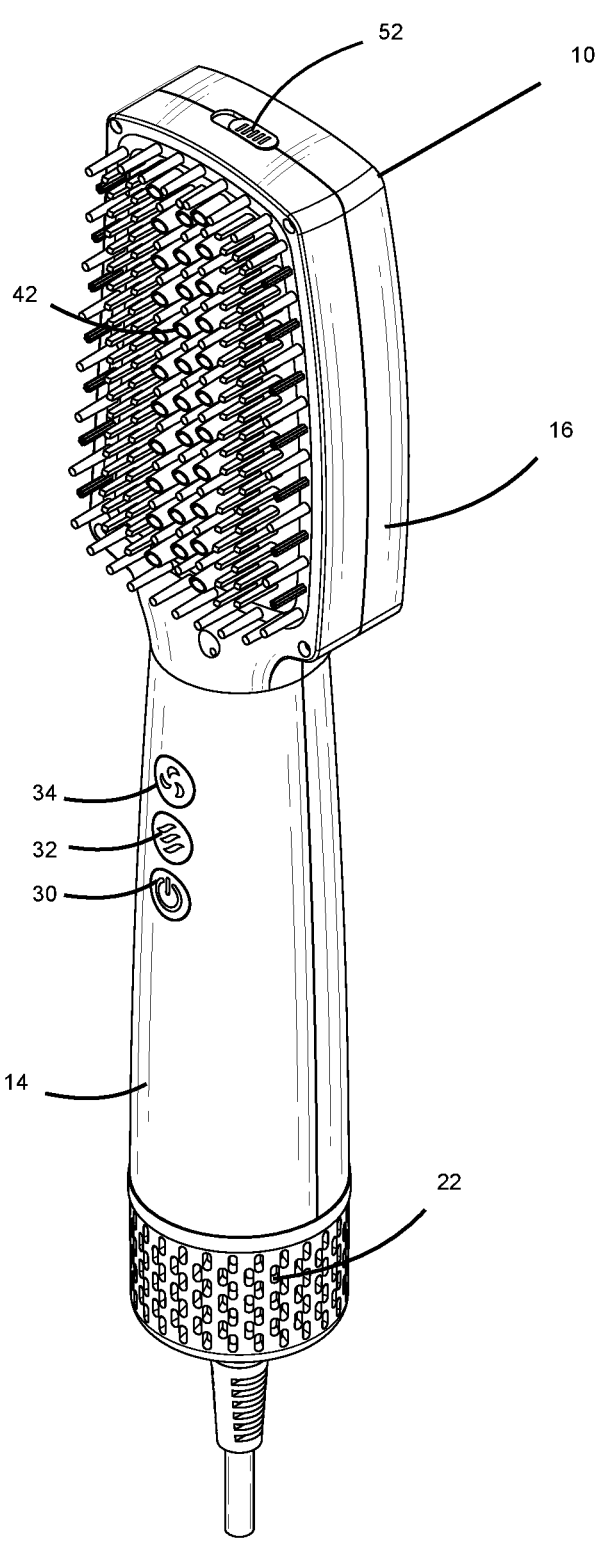
FIG. 1 is a perspective view of an embodiment of the invention.
Figure 2:
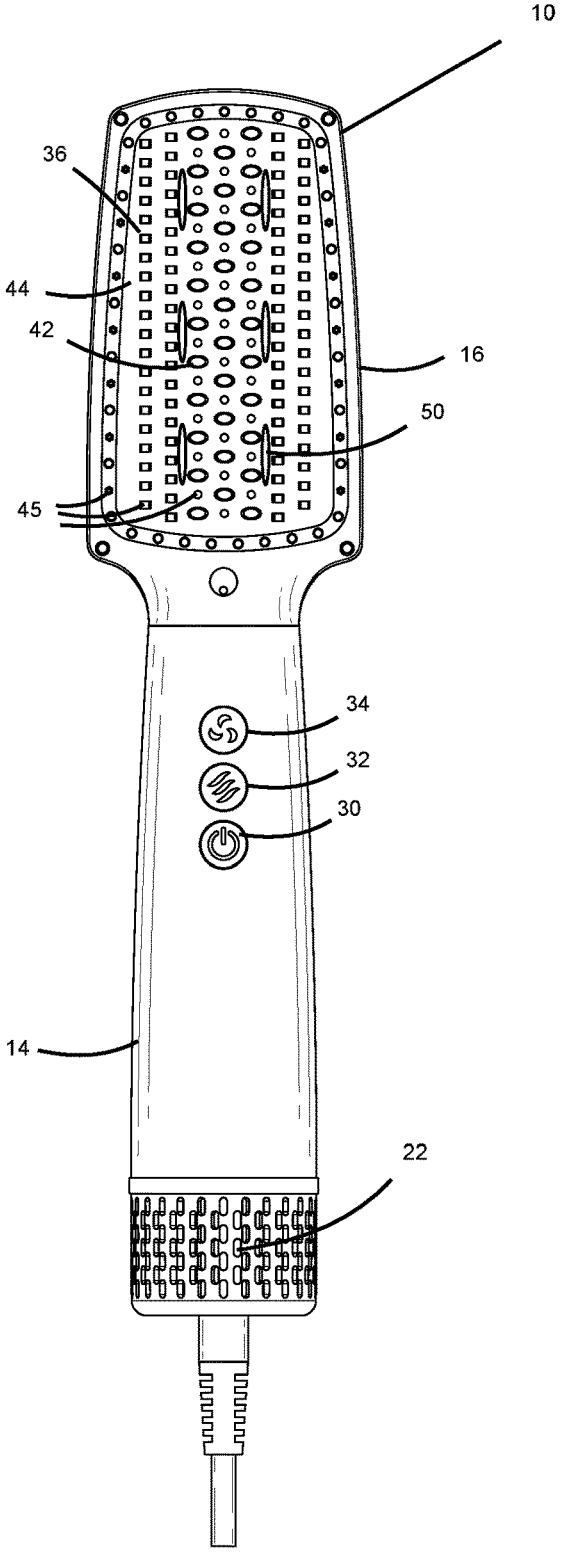
FIG. 2 is a front view of an embodiment of the invention.
Figure 3:
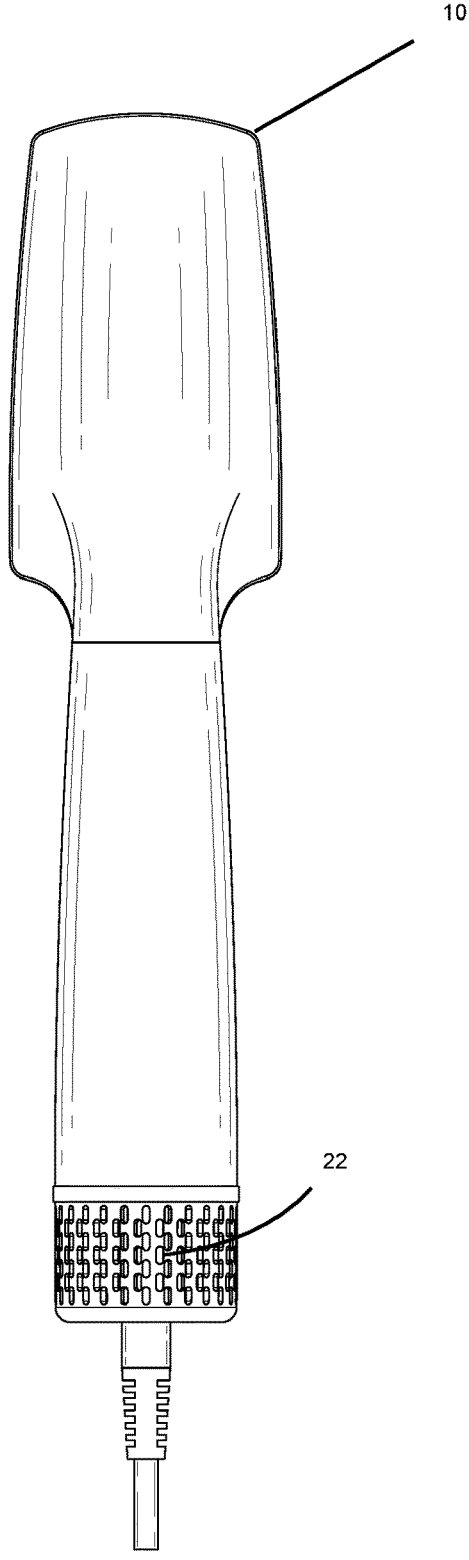
FIG. 3 is a back view of an embodiment of the invention.
Figure 4:
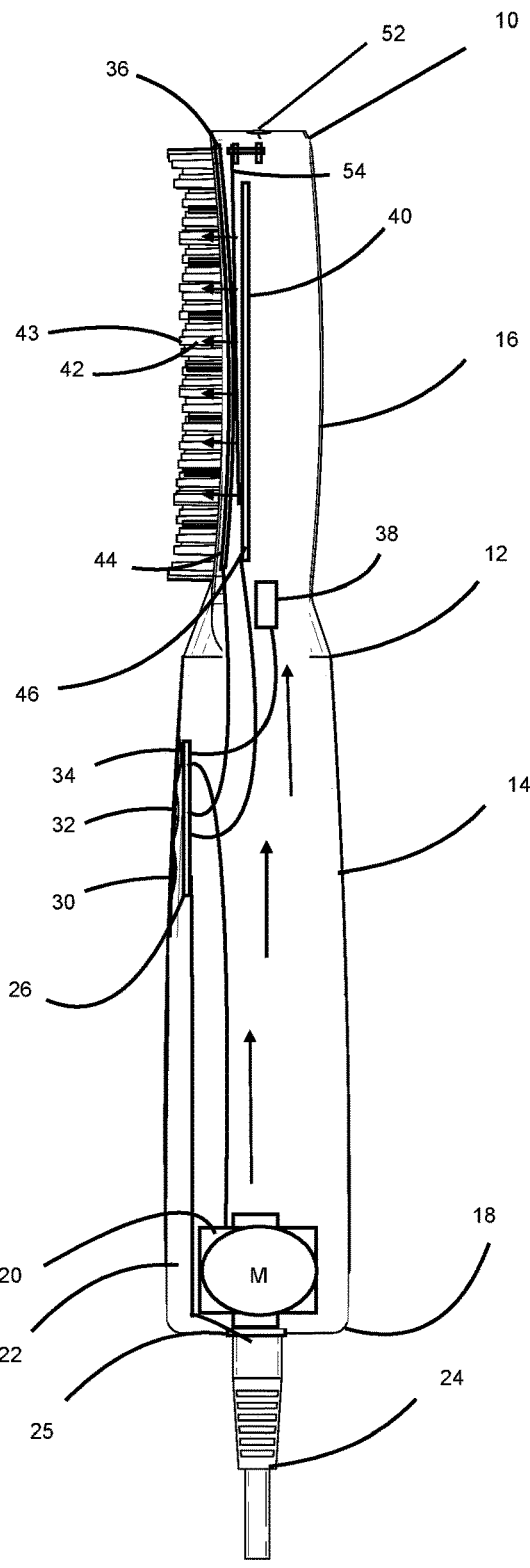
FIG. 4 is a side view revealing internal components of an embodiment of the invention.
Figure 5:
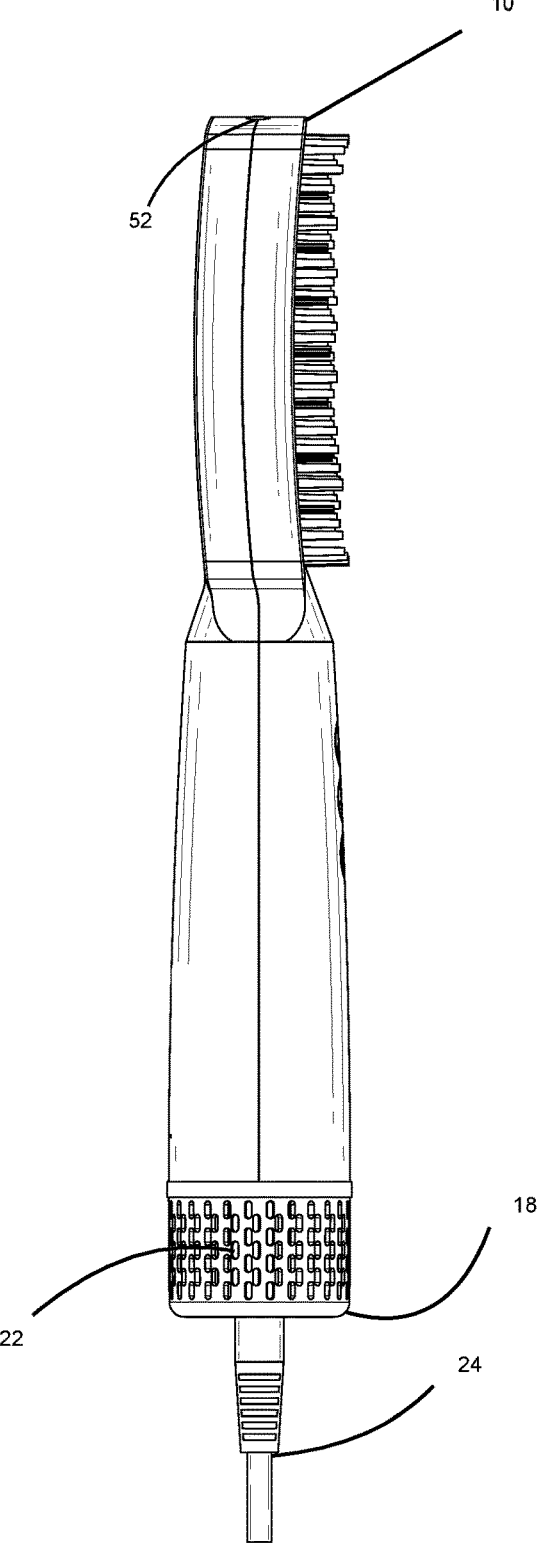
FIG. 5 is a side view of an embodiment of the invention.
Figure 6:
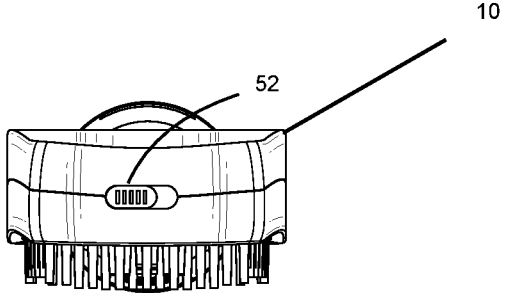
FIG. 6 is a top end view of an embodiment of the invention.
Figure 7:
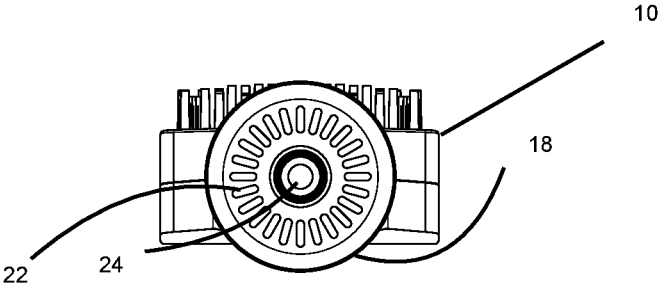
FIG. 7 is a bottom end view of an embodiment of the invention.

Referring now to the drawings, an embodiment of the invention includes a brush 10, particularly, a hair brush in accordance with the invention. The brush 10 includes a hollow housing 12 having a handle 14 and a brush head 16 extending therefrom.

Within the housing 12, shown here near an end 18 of handle 14 is a blower fan 20. The end 18 includes a plurality of orifices 22 to permit air intake for the blower fan 20. A power cord 24 connects through a swivel type connection 25 through the end 18 to a control switch panel 26. The control switch panel 26 has an on/off power button 30, a heater activation on/off button 32 and a fan on/off button 34. The control switch panel 26 provides for variable and selective settings, for example, off, low, medium and high function for the blower fan 20, heat settings when the blower fan 20 is activated low at 175° F., Medium 215° F. and high 245° F. and when the blower fan is inactive low at 280° F., Medium 355° F. and high 430° F. The control switch panel 26 is also equipped with a predetermined timed auto-shut off, such as 60 minutes.

Accordingly, the head 16 is equipped with a heating element 36 which connects to the heater activation on/off button 32. A negative ion generator 38 is operably disposed in an air flow path to deliver a negative ion airflow. The negative ion generator 38 can include positive and negative electrode array configuration such as a single sheet of metal by extrusion or punching such that the surface of the annular-like electrodes is smooth and continuous through the opening through which the air flows. The blower fan 20 creates airflow to move the negative ions through the housing 12.

A light source 40, which can include light emitting device and/or laser, can be operably disposed within the head 16 to direct light outward toward a plurality of hollow bristles 42 with open ends which extend upward from a surface 44 of the head 16. The bristles 42 are open to receive at least a portion of light therethrough. There are also a number of bristles 45 of various shapes and sizes extending from the surface 44 of the head 16. A feature is that the light emitted from a terminal end 43 the bristles 42 gets to the scalp and is not obscured by hair which can prevent the light getting to the root follicle. By virtue of this aspect of the disclosure, light is emitted with minimal obstruction to the intended target. There are also provided on the surface 44 a plurality of slotted surfaces 50 which permit air flow out of the housing area 46. A slider switch 52 can manually actuate a baffle mechanism 54 to restrict air flow through the bristles 42 per a user's personal preference. Another aspect is to provide a heating element in the head 16 and blower fan 20 operably connected to the brush 10 to direct air flow through hollow bristles 42 extending from the head 18. In a preferred embodiment, the brush 10 is equipped to enable the selective amount of air flow through the bristles 42. Another aspect of the brush 10 of the present invention is its ability to straighten hair of any length. The brush 10 of the present invention can straighten hair from the roots without burning the scalp and also can provide direct targeted application of light and heated air to the scalp as desired. The brush 10 can straighten hair and lock in moisture without causing frizzing. The brush 10 can also deliver targeted negative ions through the hollow bristles providing additional anti-static treatment to the hair and improved shine. The selective functions in heat, light, air flow and negative ion application provide a dynamic and versatile tool for hair drawing and styling. Thus, the several aforementioned objects and advantages of the present invention are most effectively attained. Those skilled in the art will appreciate that numerous modifications of the exemplary embodiment described herein above may be made without departing from the spirit and scope of the invention. Although various exemplary embodiments of the present invention has been described and disclosed in detail herein, it should be understood that this invention is in no sense limited thereby and the claims should be afforded modifications, improvements and derivations reasonably ascertainable to those skilled in the art.

What is claimed is:

1. A brush comprising:

a housing comprising a handle and a head;

a light emitting device disposed within the head to emit an application light therefrom;

a blower in said housing for creating air flow within the housing; and a plurality of hollow bristles extending from a surface of the head, each hollow bristle comprising first and second open ends wherein the first open end receives at least a portion of the application light and at least a portion of the air flow to emit out of the second open end.

2. The brush of claim 1, wherein the light emitting device comprises an infra-red light emitter.

3. The brush of claim 1, wherein the light emitting device comprises a laser.

4. The brush of claim 1, wherein the light emitting device is positioned to emit at least a portion of the application light directly through each of the plurality of the hollow bristles.

5. The brush of claim 1, wherein the blower is disposed within the handle.

6. The brush of claim 5, further comprising a control switch comprising an on/off power button, a heater activation on/off button and a fan on/off button.

7. The brush of claim 6, further comprising a slider switch and a baffle mechanism to adjust air flow to the hollow bristles wherein the slider switch actuates the baffle mechanism.

8. The brush of claim 1, further comprising one or more openings in the surface which permit air flow out of the housing.

9. The brush of claim 1, further comprising a heating element disposed within the housing between the blower and the plurality of hollow bristles.

10. The brush of claim 9, wherein the heating element is disposed between the light emitting device and the plurality of hollow bristles.

11. The brush of claim 1, further comprising a negative ion generator disposed within the housing.

* * * * *